United States Patent [19]
Hubbell et al.

[11] Patent Number: 5,481,927
[45] Date of Patent: Jan. 9, 1996

[54] VAPOR PORT AND GROUNDWATER SAMPLING WELL

[75] Inventors: Joel M. Hubbell; Allan H. Wylie, both of Idaho Falls, Id.

[73] Assignee: Lockheed Idaho Technologies Company, Idaho Falls, Id.

[21] Appl. No.: 126,471

[22] Filed: Sep. 24, 1993

[51] Int. Cl.$^6$ .......................... E21B 43/04; G01N 1/22; G01N 1/26; G01N 1/16
[52] U.S. Cl. .................. 73/863.71; 73/863.23; 73/863.32; 166/51; 166/313; 166/264
[58] Field of Search .............. 73/155, 153, 152, 73/863.71, 863.83, 864.34, 864.73, 863.32, 863.23; 166/51, 369, 292, 264, 313

[56] References Cited

U.S. PATENT DOCUMENTS

| | | | |
|---|---|---|---|
| 4,565,086 | 1/1986 | Orr, Jr. | 175/40 |
| 4,593,760 | 6/1986 | Visser et al. | 166/313 |
| 4,625,803 | 12/1986 | Walhaug et al. | 166/313 |
| 4,660,639 | 4/1987 | Visser et al. | 166/313 |
| 4,759,227 | 7/1988 | Timmons | 73/864.34 |
| 5,031,540 | 7/1991 | Kenny | 166/299 |
| 5,099,917 | 3/1992 | Roser | 166/51 |
| 5,161,613 | 11/1992 | Jones | 166/313 |
| 5,190,108 | 3/1993 | Mansuy | 166/313 |

OTHER PUBLICATIONS

Higgs, B. D., et al, "Unsaturated-Zone Vapor Port Installation in Groundwater Monitoring Wells at the Radioactive Waste Management Complex, Idaho National Engineering Laboratory," *Fourth National Technology Information Workshop, Remediation & Characterization II*, May 11–13, 1993.

Primary Examiner—Robert J. Warden
Assistant Examiner—Hien Tran
Attorney, Agent, or Firm—Hopkins Roden Crockett Hansen & Hoopes; Alan D. Kirsch

[57] ABSTRACT

A method and apparatus has been developed for combining groundwater monitoring wells with unsaturated-zone vapor sampling ports. The apparatus allows concurrent monitoring of both the unsaturated and the saturated zone from the same well at contaminated areas. The innovative well design allows for concurrent sampling of groundwater and volatile organic compounds (VOCs) in the vadose (unsaturated) zone from a single well, saving considerable time and money. The sample tubes are banded to the outer well casing during installation of the well casing.

15 Claims, 6 Drawing Sheets

VAPOR PORT AND GROUNDWATER SAMPLING WELL

CONTRACTUAL ORIGIN OF THE INVENTION

EG&G Idaho, Inc. has rights in this invention pursuant to Contract No. DE-AC07-76ID01570 between the United States Department of Energy and EG&G Idaho, Inc.

BACKGROUND OF THE INVENTION

1. Field of the Invention

This invention relates to an underground well having multiple vapor sample ports in a vadose zone and a sampling pump and pipe for groundwater samples within a common casing.

2. Discussion of the Prior Art

Currently, groundwater and vadose vapor zone contamination monitoring wells are separate installations for remedial actions and characterization of subsurface contamination.

U.S. Pat. No. 4,565,086 issued to Orr on Jan. 21, 1986, discloses an apparatus and method for detecting the level of gases entrained within a circulating drilling fluid used in subterranean well operations. Detection of incipient gas kicks during drilling operations is accomplished by detecting the level of entrained gases. A gas-air sample is gathered at the surface of the well, and a gas-air sample having a constant relative humidity is delivered at a constant volumetric flow rate to gas sensors. Dilution air is automatically added to the sample when the gas concentrations exceed a known limit.

SUMMARY OF THE INVENTION

Generally speaking, the invention is an apparatus for sampling and extracting underground vapors and also pumping groundwater contained in a single well within a borehole comprising:

- a casing within the borehole having a diameter less than the borehole, thereby forming an annular space;
- a multiplicity of vapor sampling tubes banded to an outside of the casing, said sampling tubes having a plurality of small sample ports at a bottom portion of the tubes;
- a groundwater casing having a groundwater pipe within, said groundwater pipe having a water pump at a bottom section of the groundwater pipe, said pump for lowering the adjacent water table;
- an annular ring of sand adjacent the sample ports, said sand having a diameter greater than the sample ports;
- an upper annular sealing ring above the ring of sand and a lower annular sealing ring below the ring of same;
- an upper annular ring of grout above the upper sealing ring and a lower annular ring of grout below the lower sealing ring; and
- wherein the sampling tubes may be pressurized or evacuated from a surface of the well thereby pumping air down to the sample ports or providing vapor sample at the well surface.

This invention has a different objective and apparatus from the prior art and allows monitoring of the groundwater and also sampling (extraction) of volatile organic compounds (VOC) at multiple locations above and below the water table after the well has been drilled.

Other objects, advantages, and capabilities of the present invention will become more apparent as the description proceeds.

DETAILED DESCRIPTION OF THE INVENTION

Figure 1:
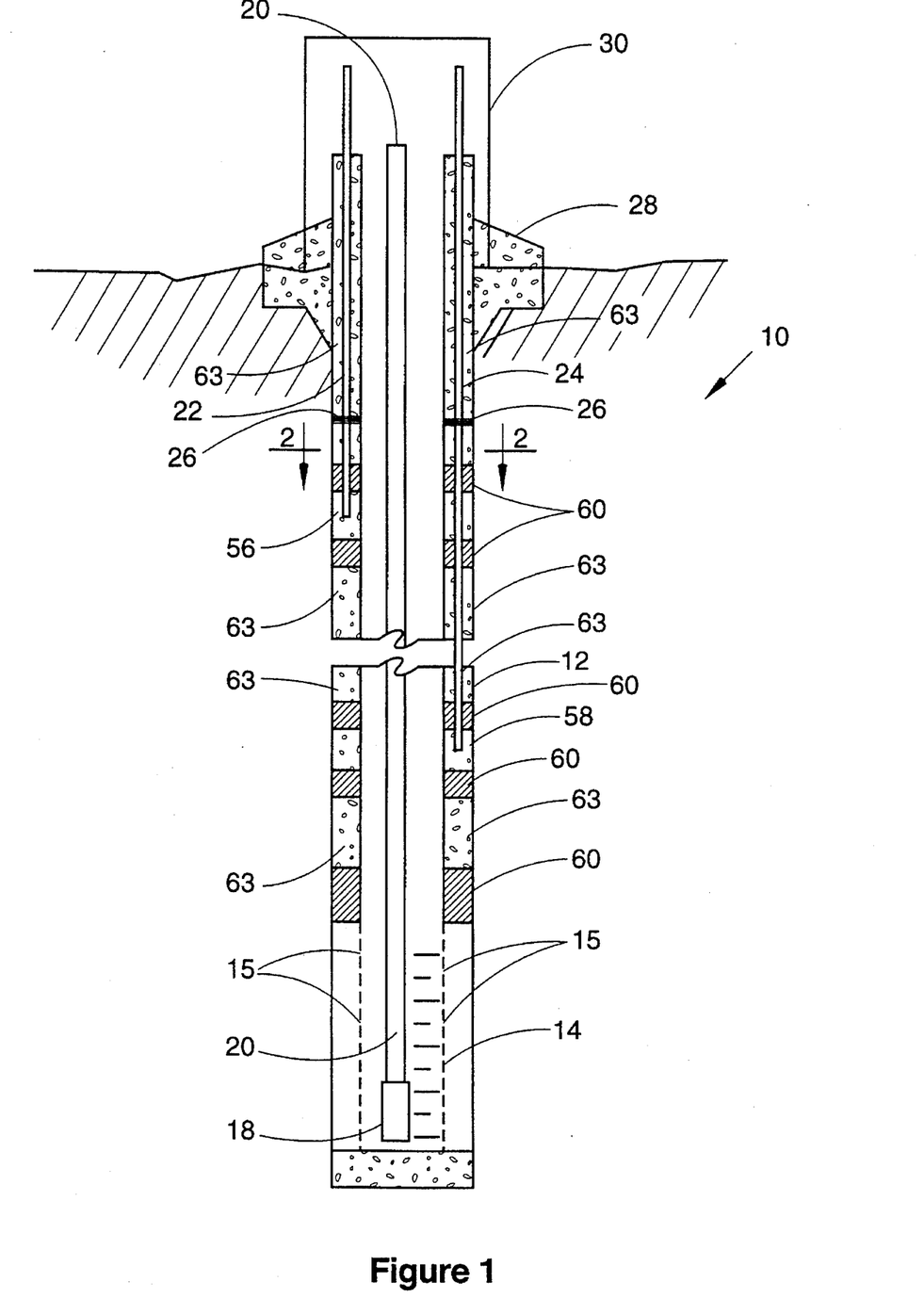
FIG. 1 is a partial front-section view of the sampling well of the present invention.

FIG. 1 illustrates in partial elevation and section view the sampling well 10 of the present invention. The sampling well is contained within borehole 12 and consists of an outer metal or plastic pipe casing 14 having a bottom screen section 15, which contains a water pump 18 and riser pipe 20.

The ⅜-inch gas sample tubes 22 and 24, whose sizes are determined by sampling requirements, are strapped or clamped to the outer circumference of the casing 14 by bands 26 (FIG. 2) at about 10-foot intervals. At the top of the casing is a cement pad 28 and metal locking cap 30.

Figure 2:
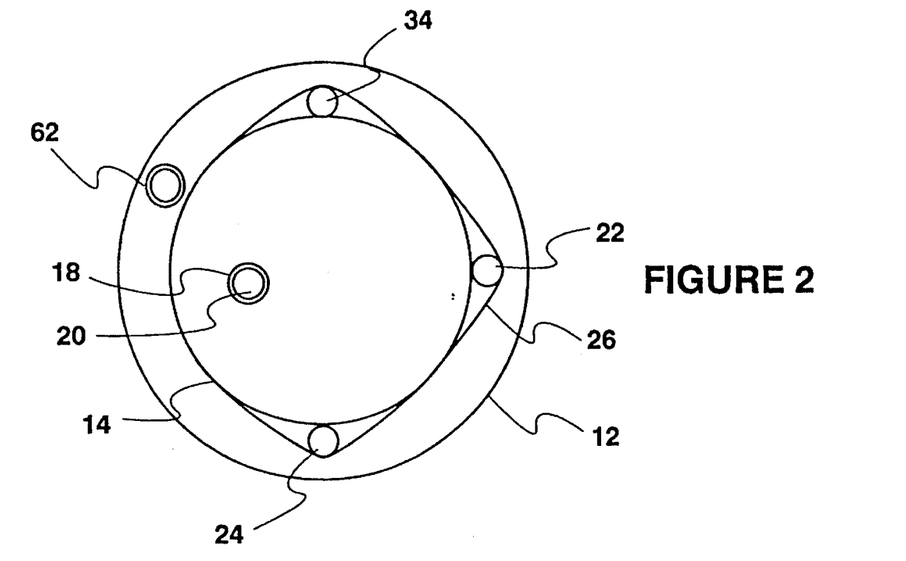
FIG. 2 is a top section view of the well taken along lines 2—2 of FIG. 1.

Referring to FIG. 2 cross-section, the piezometer tube 32 (pressure sensor) is also contained within the casing 14, and the strap 26 can be seen banding the gas sample tubes 22, 24, and 34 to the casing 14 which are all within 8-inch borehole 12.

Figure 3:
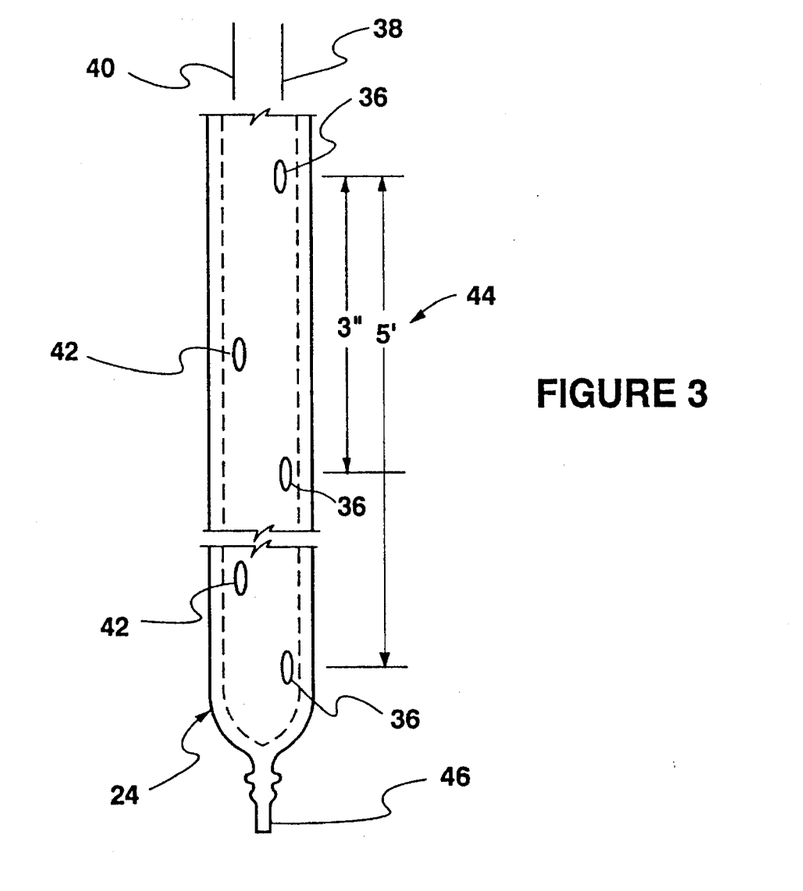
FIG. 3 is a front elevation view of the gas sample tube of the present invention.

A detail of the 1/16-inch sampling ports can be seen in FIG. 3. The sample ports 36 are located in a first vertical column 38 at about 3 -inch intervals. A second vertical column 40, 90° around the circumference, contains another set of sample ports 42. The overall vertical sample port length is about 5 feet as at 44, and the tube is crimped at the bottom 46 to seal the tube 24.

Figure 4:
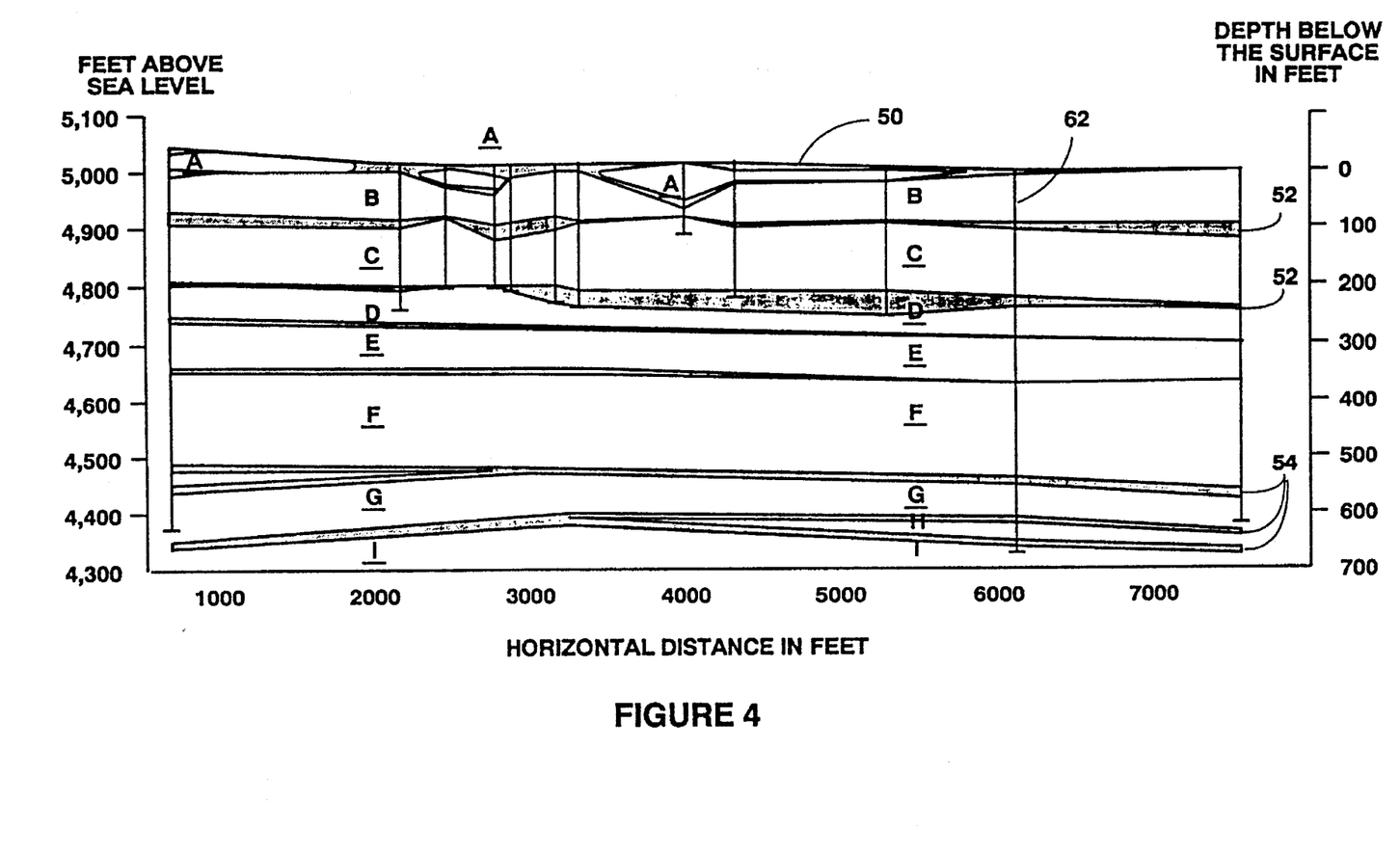
FIG. 4 is a stratigraphic section view of a sampling borehole and the typical locations of the gas sample ports.

The process of drilling the well and installing the piping and sample ports will be described by referring to FIGS. 1 and 4. FIG. 4 illustrates the stratigraphic cross-section of an east-west line at the Radioactive Waste Management Complex (RWMC) within the Idaho National Engineering Laboratory (INEL) where about 10 wells were drilled and/or sampled.

The geology around the RWMC is extremely complex and heterogeneous, making tracking of contaminant migration difficult. The general stratigraphic framework of the RWMC area is characterized by a thin layer of unconsolidated surficial sediment at 50, basaltic lava flows A through I, and thin sedimentary interbeds 52 and 54 composed of loess, eolian sand, alluvial sand and gravel, and lacustrine deposits. Interbeds were deposited during quiescent periods of volcanic activity. The unsaturated zone (above the water table) consists of at least 22 basaltic lava flow units and seven sedimentary interbeds. The lava flows compose approximately 90–95 percent of the 700-foot thick stratigraphic sequence that is penetrated by most RWMC wells. The basalts are subdivided into 10 lava flow groups and separated by sedimentary interbeds. Seven of the lava flow groups A through H and three interbeds E, F, and G are fairly continuous beneath the RWMC area. The two major interbeds 52 in the vadose zone in the vicinity of the RWMC are located approximately 110 feet and 240 feet below land surface.

A volatile organic compound (VOC) vapor plume in the vadose zone in the vicinity of the RWMC is apparently migrating from some of the waste buried in the subsurface disposal area (SDA). The exact extent, location, and concentrations making up this plume are unknown due to the limited spatial distribution of existing vapor ports. Six monitoring wells were installed as part of a groundwater investigation. An opportunity also existed to use the existing boreholes for two purposes: groundwater sampling and vadose zone vapor sampling. Vapor port installation would significantly aid in understanding the vapor plume in the unsaturated zone.

A plan was conceived to install vapor ports in the annular space of the groundwater wells. Since the groundwater monitoring wells fully penetrate the approximately 600 feet of vadose zone, vapor ports could be installed at any depth above the water table. The plan was implemented in the summer of 1992.

Drilling in the Snake River Plain basalts is treacherous due to the fractured nature of the basalt and the caving of the sedimentary interbeds. Boreholes are stabilized by grouting and redrilling the sloughing zone. The drawback to grouting for borehole stabilization is that the grout fills all of the void space and may adversely affect the permeability of the grouted area.

During drilling, all grouted zones were carefully recorded. Upon completion of drilling and before well completion, the boreholes were characterized with geophysical and video logs. Logs from the geologists, drillers, and geophysical equipment were studied to determine vapor port placement. Highly fractured zones, rubble zones, and areas of presumed high permeability were targeted for installation of vapor ports because the dense basalt has a very low are permeability. For obvious reasons, grouted zones were avoided; and zones of high permeability and areas directly above sedimentary interbeds, e.g., at 52 and 54 (FIG. 4), were selected for vapor port placement. Zones above sedimentary interbeds were selected because it has been suggested that the sedimentary interbeds act as confining or retardation layers for vertical migration of organic compounds.

After a well was drilled, logged, and the vapor port depths were selected, the drill location was set up for completion. A drum with dividers held the spools of stainless steel tubing. When the casing was lowered into the well to where the lowest first targeted vapor probe depth at 58 (FIG. 1), the first strand of tubing 22 was attached to the casing. As the casing was lowered into the well, the tubing was spooled off the drum through the drill rig's pipe rack (or carousel) and was lowered with the casing.

In the immediate area of the vapor port intake and filter pack, the tubing was attached to the outer casing 12 with banding 26. The remaining casing with vapor ports was lowered down the borehole until all of the downhole equipment was added at the specified depths.

To isolate each of the zones being sampled, the immediate area around the sampling port was filter packed with size 8–10 grit silica sand or other permeable material as at 56 and 58. This size ensured that no sand would enter the tubing through the $\frac{1}{16}$-inch holes 36 and 42 (FIG. 3) and avoided the need for screen or mesh covering the holes. Above and below each filter pack, the borehole was sealed with bentonite 60. Bentonite is a colloidal clay which has high swelling capacity in water and can seal off the vertical sections of the borehole. The bentonite would also seal the port from moisture which might enter the filter pack.

Above and below the bentonite seal, the annular space 63 was grouted or sealed with an impermeable material. All completion materials were installed through tremie pipe 62 (FIG. 2) outside the casing 14 to ensure that no residual materials stuck to the borehole walls.

Nineteen vapor sampling ports were installed in the vadose zone in six groundwater wells as part of the monitoring well installation effort. All 19 of the vapor ports are open and available for sampling due to the methodology used. Gas samples have been collected from the 19 ports, and invalidated data show that the vapor from each port contains some hazardous constituents, thereby greatly increasing the knowledge of the vapor plume in the vadose zone. A 700-foot well with multiple sample levels is shown at 62 in FIG. 4.

Figure 5:
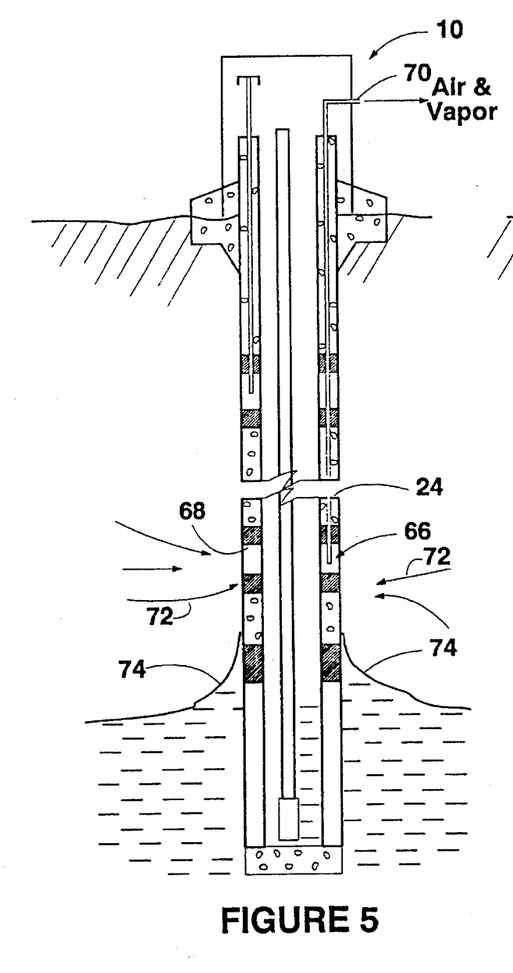
FIG. 5 is a partial front-section view of the well during vapor sampling.

The well apparatus as described above can also be used for vapor extraction (remediation) and groundwater sampling in a single well as shown in FIG. 5. In this case, the vapor port portion 66 of the well 10 could be enlarged by using larger tubing 24 and increasing the depth of the annular ring 68 of sand. Air would be evacuated at the tube 70 causing vapor flow 72 into vapor port portion 66. The effect of this vacuum causes concave water surface 74.

Figure 6:
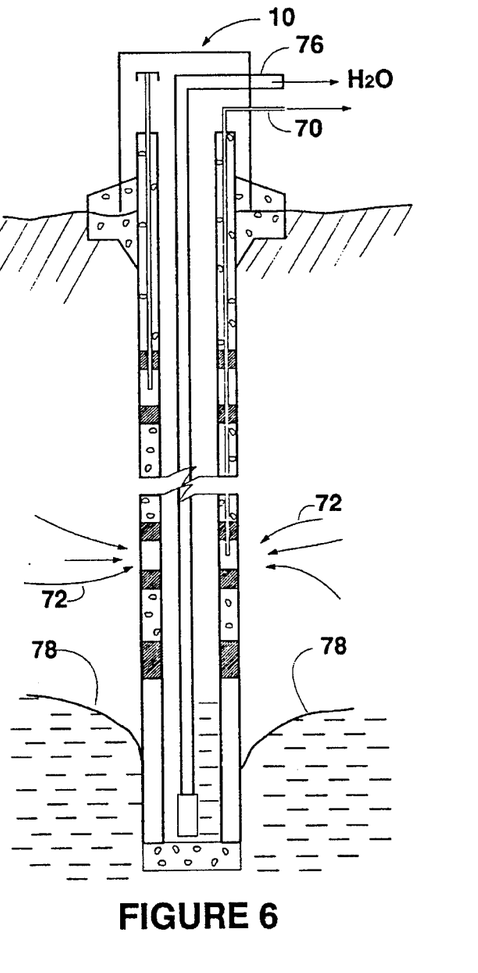
FIG. 6 is a partial front-section view of the well during vapor sampling and groundwater pumping.

Referring to FIG. 6, groundwater can be pumped out at pipe 76 while air is evacuating at 70 creating the convex water table surface 78.

Figure 7:
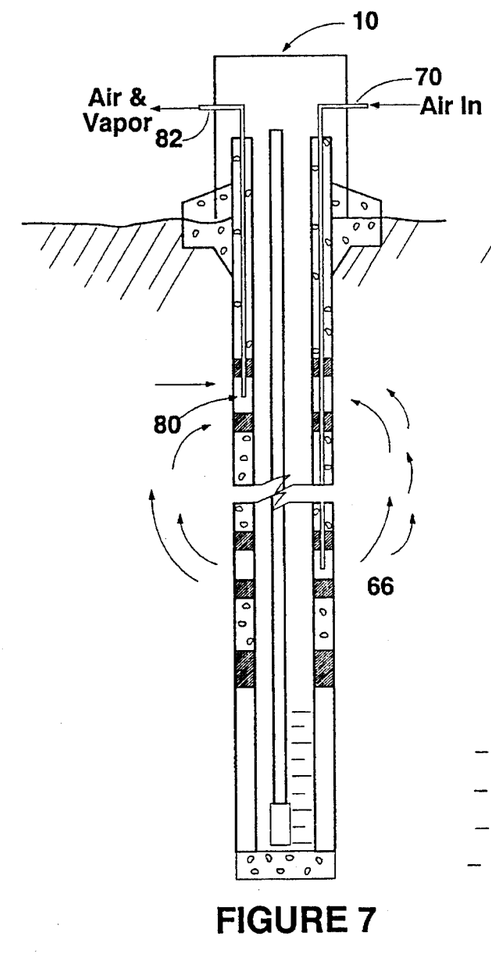
FIG. 7 is a partial front-section view of the well during air purging and sampling.

In yet another application, the well apparatus can be used to produce vertical flow paths in ground conditions where there are no intervening impermeable basalt or other layers. Referring to FIG. 7, the device can be used to perform vapor extraction at multiple depths in a well to perform intrawell vapor extraction/injection. Vapor ports 66 and 80 could be placed at multiple depths in a well and used to flush air from one depth to another for removing VOC's adjacent at the well. The air flow paths can be reversed to enhance the extraction process or the air flow oscillated (turned on and off) to enhance biodegradation or to reduce overall pumping time (to allow diffusion) by injecting air at 70 and removing air and vapor at 82.

Figure 8:
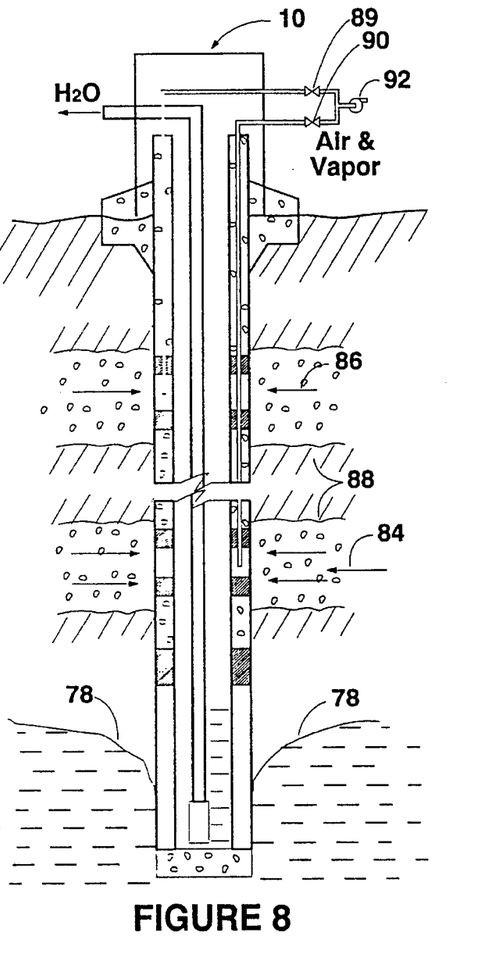
FIG. 8 is a partial front-section view of the well during selective air sampling and groundwater pumping.

A common problem in underground vapor extraction systems is having low and high permeability strata at different levels. FIG. 8 identifies at low permeability stratum at 84 and a high permeability stratum at 86 separate by impermeable layer(s) 88. The air and vapor flow rates at levels 84 and 86 can be regulated by selective operation of valves 89 and 90 at the vacuum pump 92 to optimize vapor removed from soil adjacent to the well 10.

Figure 9:
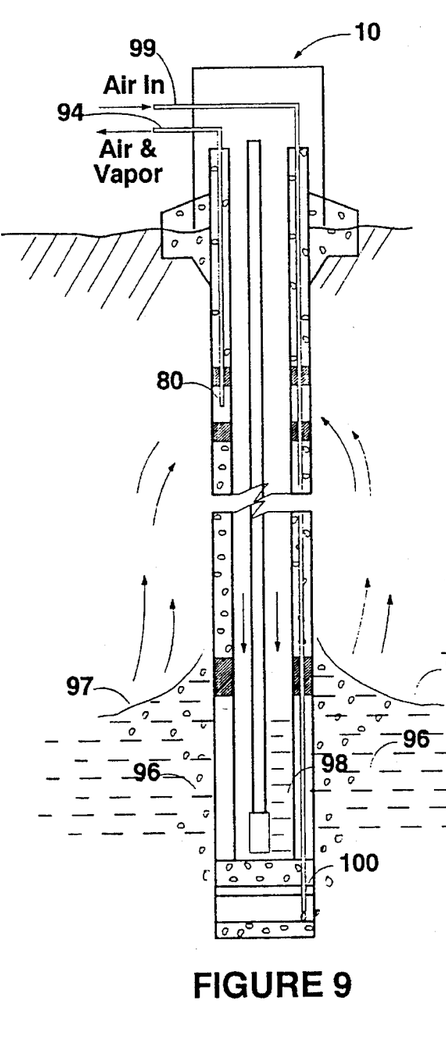
FIG. 9 is a partial front-section view of the well during air sparging.
Figure 10:
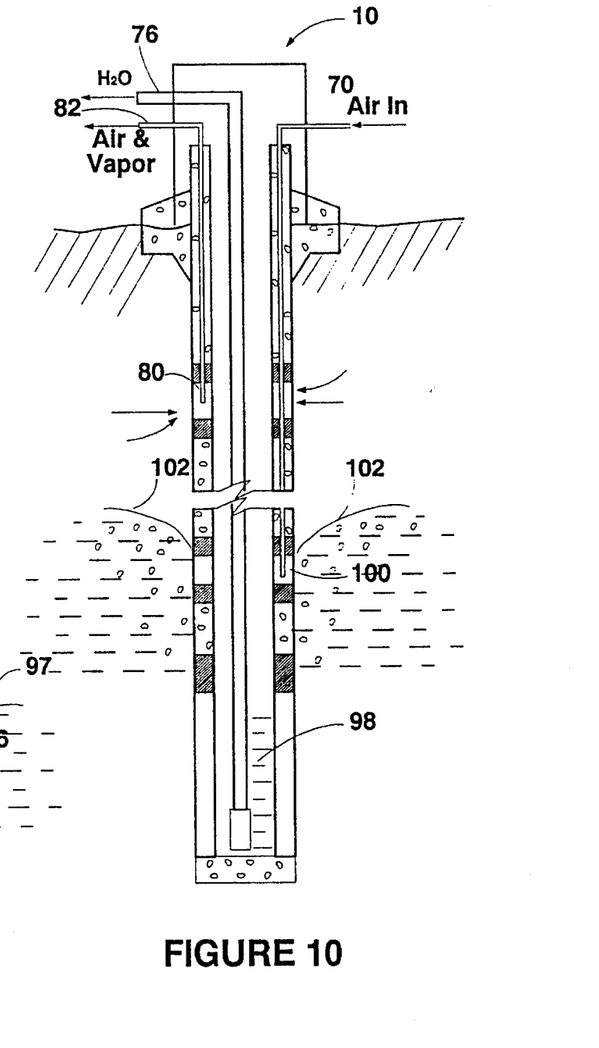
FIG. 10 is a partial front-section view of the well during air sparging and groundwater pumping.

The well apparatus 10 of FIG. 9 can perform both air extraction at pipe 94 and sparging air 96 in the same well (sparging involves injecting air below the water table 97 to remove VOC's from groundwater). Air is injected at 99 and into vapor port 100 of the well while the upper vapor extraction ports 80 of the well remove the organic vapors. Conversely, a "vapor port" could be placed below the water table 102 as in FIG. 10 for air injection (sparging), producing a well that could air sparge the lower portion of the well, pump groundwater at screened interval 98 out pipe 76 for treatment at land surface and extracting the sparged vapors from the vadose zone at port 80, all operations using a single well.

For all the scenarios listed above, the additional vapor ports in the vadose zone that are not actively being used could be used to monitor vapor concentrations or pressure changes adjacent to the well. The combination of vapor port and monitoring well installation is a cost effective and technically feasible approach to concurrently characterizing groundwater and organic plumes in the vadose zone. Sampling data from the vapor ports will provide useful information for determining the lateral and vertical extent of organic vapor plumes in the subsurface.

While preferred embodiments of the invention have been disclosed, various modes of carrying out the principles disclosed herein are contemplated as being within the scope of the following claims. Therefore, it is understood that the scope of the invention is not to be limited except as otherwise set forth in the claims.

What is claimed is:

1. A system for extracting underground vapors and groundwater from a single well within a borehole extending downward from the earth surface, comprising:
    a. a casing extending downward from the earth surface within a borehole, said casing having a diameter less than the borehole, thereby forming an annular space between the casing and the borehole, and the casing having a bottom screened section;
    b. a multiplicity of vapor tubes extending downward from the earth surface within said annular space, each of said tubes having a plurality of ports at a bottom portion of the tubes and an upper portion of each of said tubes being attached to vacuum means located on the earth surface for extracting underground vapors through said tubes to the earth surface;
    c. a riser pipe within the casing, said riser pipe having a water pump at a bottom section of the riser pipe for pumping groundwater surrounding said borehole through said bottom screened section of the casing;
    d. an annular ring of permeable material within said annular space at an underground depth substantially equal to the depth of the plurality of ports at the bottom portion of said tubes, said permeable material having a particle size greater than the ports;
    e. an upper annular sealing ring of substantially impermeable material above the annular ring of permeable material and a lower annular sealing ring of substantially impermeable material below the annular ring of permeable material, said upper and lower annular sealing rings providing a water and vapor seal within the annular space above and below the annular ring of permeable material.

2. The system of claim 1 wherein the sealing rings of impermeable material are formed from colloidal clay.

3. The system of claim 2 wherein the colloidal clay is bentonite.

4. The system of claim 1 wherein the permeable material is sand.

5. The system of claim 1 further comprising bands for attaching the vapor tubes to the casing.

6. The system of claim 1 wherein the impermeable material is grout.

7. The system of claim 1 wherein the permeable material is gravel.

8. A process for removing underground vapor and water from a single well within a borehole comprising the steps of:
    (a) establishing a borehole extending downwardly from the surface of the ground to a depth below water table;
    (b) placing a casing within said borehole so that an annular space is formed between said casing and said borehole, the casing having a riser pipe within said casing, the riser pipe extending downwardly from the surface of the ground and having a pump at a lower end of the riser pipe;
    (c) placing a plurality of tubes within said annular space, said tubes extending downwardly through the annular space, each of said tubes having a plurality of ports at different depths within said annular space;
    (e) providing an annular ring of permeable material within said annular space at each of the depths different of the plurality of ports;
    (f) providing an annular ring of impermeable material above each of said annular rings of permeable material and providing an annular ring of impermeable material below each of said annular rings of permeable material, said annular ring of impermeable material creating a water and vapor seal above and below the respective annular ring of permeable material;
    (g) extracting underground vapors through said plurality of ports and transporting said underground vapors to the surface of the ground through said tubes and extracting underground water through said pump to the surface of the ground through said riser pipe.

9. The process of claim 8 wherein said impermeable material is colloidal clay.

10. The process of claim 8 wherein said impermeable material is bentonite.

11. The process of claim 8 wherein said permeable material is sand.

12. The process of claim 8 wherein said permeable material is gravel.

13. The process of claim 8 wherein air from the ground surface is injected underground through some of said ports and the underground vapors are extracted through the remaining ports.

14. The process of claim 13 wherein the air is injected below the water table to sparge the underground water to create the underground vapors which are extracted.

15. A system for extracting underground vapors and groundwater from a single well within a borehole extending downward from the earth surface, comprising:
    a. a casing extending downward from the earth surface within a borehole, said casing having a diameter less than the borehole, thereby forming an annular space between the casing and the borehole, and the casing having a bottom screened section;
    b. a multiplicity of vapor tubes extending downward from the earth surface within said annular space, each of said tubes having a plurality of ports located at different depths along the vapor tubes and an upper portion of each of said tubes being attached to vacuum means located on the earth surface for extracting underground vapors through said tubes to the earth surface;
    c. a riser pipe within the casing, said riser pipe having a water pump at a bottom section of the riser pipe for pumping groundwater surrounding said borehole through said bottom screened section of the casing;
    d. an annular ring of permeable material within said annular space at each of the different depths of the plurality of ports of said tubes, said permeable material having a particle size greater than the ports;

e. an upper annular sealing ring of substantially impermeable material above each of the annular rings of permeable material and a lower annular sealing ring of substantially impermeable material below each of the annular rings of permeable material, said upper and lower annular sealing rings providing a water and vapor seal within the annular space above and below the respective annular ring of permeable material.

* * * * *